United States Patent
Seedhom

(10) Patent No.: US 10,155,068 B2
(45) Date of Patent: Dec. 18, 2018

(54) CONNECTIVE TISSUE REPAIR TECHNOLOGY

(71) Applicant: Xiros Limited, Leeds, Yorkshire (GB)

(72) Inventor: Bahaa Botros Seedhom, Leeds (GB)

(73) Assignee: Xiros Limited, Yorkshire (GB)

( * ) Notice: Subject to any disclaimer, the term of this patent is extended or adjusted under 35 U.S.C. 154(b) by 0 days.

(21) Appl. No.: 14/168,848

(22) Filed: Jan. 30, 2014

(65) Prior Publication Data

US 2014/0222162 A1    Aug. 7, 2014

(30) Foreign Application Priority Data

Feb. 1, 2013 (GB) .................................. 1301784.3

(51) Int. Cl.
*A61F 2/02* (2006.01)
*A61L 27/38* (2006.01)
(Continued)

(52) U.S. Cl.
CPC ...... *A61L 27/3804* (2013.01); *A61F 2/30756* (2013.01); *A61L 27/3817* (2013.01);
(Continued)

(58) Field of Classification Search
CPC ..................................... A61F 2/30756; A61F 2002/30757–2002/30766;
(Continued)

(56) References Cited

U.S. PATENT DOCUMENTS

| 4,546,769 A | 10/1985 | Planck et al. |
| 4,839,215 A | 6/1989 | Starling et al. |

(Continued)

FOREIGN PATENT DOCUMENTS

| EP | 0 145 492 A2 | 6/1985 |
| EP | 0 744 162 A2 | 11/1996 |

(Continued)

OTHER PUBLICATIONS

"Entangle." Merriam-Webster.com. Merriam-Webster,n.d. Web. May 1, 2016 from http://www.merriam-webster.com/dictionary/entangle.*

(Continued)

*Primary Examiner* — Katrina Stransky
*Assistant Examiner* — Kankindi Rwego
(74) *Attorney, Agent, or Firm* — Stoel Rives LLP; Zhi-Xiang Oh

(57) ABSTRACT

An implantable prosthetic device for the repair of damaged cartilage including methods of implantation and repair. The prosthetic device is formed from a biocompatible pad having an open structure connected to a textile or non-woven sheet-like anchor. In one embodiment the anchor comprises legs that extend away from a perimeter region of the pad and spaced apart along their respective lengths such that an in unfolded orientation, the longitudinal edges of neighbouring legs are not in contact with one another and a spatial gap is provided between the anchoring legs. The anchor may also be provided in the form of strips to which anchorage sutures or other medical cords may be attached to fixate the device between connective tissue.

20 Claims, 13 Drawing Sheets

(51) Int. Cl.
 *A61F 2/30* (2006.01)
 *A61L 27/56* (2006.01)
 *A61F 2/00* (2006.01)

(52) U.S. Cl.
 CPC ....... *A61L 27/3843* (2013.01); *A61L 27/3852* (2013.01); *A61L 27/56* (2013.01); *A61F 2/0063* (2013.01); *A61F 2002/302* (2013.01); *A61F 2002/30153* (2013.01); *A61F 2002/30156* (2013.01); *A61F 2002/30158* (2013.01); *A61F 2002/30576* (2013.01); *A61F 2002/30909* (2013.01); *A61F 2002/30914* (2013.01)

(58) Field of Classification Search
 CPC .. A61F 2002/30759; A61F 2002/30761; A61F 2002/30762; A61F 2002/30764; A61F 2/0004; A61F 2/0009; A61F 2/0013; A61F 2/0018; A61F 2/0022; A61F 2/0027; A61F 2/0031; A61F 2/0036; A61F 2/004; A61F 2/0045; A61F 2/005; A61F 2/0054; A61F 2/0059; A61F 2/0063; A61F 2/0077; A61F 2/0081; A61B 317/0466; A61B 2017/0404; A61B 2017/0406; A61B 2017/0448
 See application file for complete search history.

(56) References Cited

U.S. PATENT DOCUMENTS

| | | | |
|---|---|---|---|
| 5,441,508 A | | 8/1995 | Gazielly et al. |
| 5,736,372 A * | | 4/1998 | Vacanti ............ A61F 2/02 424/422 |
| 6,042,534 A | | 3/2000 | Gellman et al. |
| 6,652,872 B2 * | | 11/2003 | Nevo et al. ............ 424/423 |
| 7,131,944 B2 * | | 11/2006 | Jacquetin ............ A61F 2/0045 600/30 |
| 8,109,866 B2 * | | 2/2012 | Bouchier ............ A61F 2/0045 600/30 |
| 2002/0052660 A1 | | 5/2002 | Greenhalgh |
| 2003/0023316 A1 * | | 1/2003 | Brown et al. ............ 623/23.72 |
| 2003/0212462 A1 | | 11/2003 | Gryska et al. |
| 2004/0060410 A1 | | 4/2004 | Leung et al. |
| 2004/0133275 A1 * | | 7/2004 | Mansmann ............ 623/14.12 |
| 2007/0041952 A1 | | 2/2007 | Guilak et al. |
| 2008/0207989 A1 | | 8/2008 | Kaleta et al. |
| 2008/0241213 A1 * | | 10/2008 | Chun et al. ............ 424/423 |
| 2008/0243149 A1 | | 10/2008 | Kockerling et al. |
| 2009/0138082 A1 | | 5/2009 | Reah et al. |
| 2009/0156986 A1 | | 6/2009 | Trenhaile |
| 2010/0063599 A1 | | 3/2010 | Brunelle et al. |
| 2010/0152530 A1 * | | 6/2010 | Timmer et al. ............ 600/37 |
| 2010/0179591 A1 | | 7/2010 | Saltzman et al. |
| 2011/0082479 A1 | | 4/2011 | Friedlander |
| 2011/0093073 A1 * | | 4/2011 | Gatt ............ A61F 2/30756 623/14.12 |
| 2011/0118762 A1 | | 5/2011 | Dooney, Jr. et al. |
| 2011/0125287 A1 | | 5/2011 | Hotter et al. |
| 2012/0053399 A1 * | | 3/2012 | Rao et al. ............ 600/37 |
| 2012/0095482 A1 | | 4/2012 | Peterson et al. |
| 2012/0150204 A1 | | 6/2012 | Mortarino et al. |
| 2013/0116799 A1 | | 5/2013 | Derwin et al. |

FOREIGN PATENT DOCUMENTS

| | | |
|---|---|---|
| EP | 1 537 883 A2 | 6/2005 |
| GB | 2 276 823 A | 10/1994 |
| GB | 2 342 865 A | 4/2000 |
| WO | WO 01/39694 A2 | 6/2001 |
| WO | WO 02/30324 A1 | 4/2002 |
| WO | WO 02/35990 A2 | 5/2002 |
| WO | WO 03/007847 A1 | 1/2003 |
| WO | WO 03/095609 A2 | 11/2003 |
| WO | WO 2004/010897 A1 | 2/2004 |
| WO | WO 2008/100685 A2 | 8/2008 |
| WO | WO 2013/017835 A1 | 2/2013 |
| WO | WO 2013/017836 A2 | 2/2013 |

OTHER PUBLICATIONS

Non-Final Office Action for U.S. Appl. No. 14/171,203, filed Feb. 3, 2014, and mailed from the USPTO dated March 6, 2017, 34 pgs.
Notice of Allowance and Fee(s) Due for U.S. Appl. No. 14/237,507, filed Jul. 1, 2014, and mailed from USPTO dated Apr. 14, 2017, 21 pgs.
Final Office Action for U.S. Appl. No. 14/237,507, filed Jul. 1, 2014, and mailed from the USPTO dated Nov. 17, 2016, 16 pgs.
Non-Final Office Action for U.S. Appl. No. 14/237,507, filed Jul. 1, 2014, and mailed from the USPTO dated May 3, 2016, 18 pgs.
Non-Final Office Action for U.S. Appl. No. 14/235,885, filed Apr. 28, 2014, and mailed from the USPTO dated Nov. 30, 2016, 27 pgs.

* cited by examiner

CONNECTIVE TISSUE REPAIR TECHNOLOGY

RELATED APPLICATIONS

This application claims priority to Great Britain Application No. 1301784.3, filed Feb. 1, 2013, which is incorporated by reference in its entirety.

TECHNICAL FIELD

This invention relates to methods, instruments and devices involved in the repair generally of damaged connective tissue in an animal, including a human being and in particular although not exclusively to the repair of damaged cartilage present at or on the surface of bone and in the repair of specific connective tissue damage, such as that of the rotator cuff at the shoulder joint.

BACKGROUND

With regards the repair of cartilage damage, defects in the articular surfaces of the knee joint, especially in young active individuals, are currently a focus of interest by orthopaedic surgeons. It is desirable to repair such defects in order to prevent the articular damage from spreading, thereby leading to serious degenerative changes in the joint. Such changes may result in the need for a total knee replacement which is particularly undesirable in young active individuals with a long life expectancy. If the lifetime of the implant is less than that of the patient, a revision procedure may be necessary. Preferably, such revision procedures are to be avoided, as they are considerably inconvenient to the patient and with a lower rate of success than primary procedures. Furthermore total knee revision procedures are both lengthy and very costly.

Therefore techniques are still sought to repair focal cartilage defects, particularly in young individuals to postpone, if not obviate, the need for total knee replacement. Cartilage focal defects are still, most commonly treated with microfracture technique, in which the subchondral bone plate in the defect site is pitted with a sharp pick to cause bleeding from bone marrow. This process facilitates the migration of mesenchymal progenitor cells to the defect region and subsequent tissue growth within. Although appealing because it is simple and inexpensive, the efficacy of this treatment has not been demonstrated when dealing with full thickness cartilage defects [Frisbie, D. D., Oxford, J. T., Southwood, L., Trotter, G. W., Rodkey, W. G., Steadman, J. R., Goodnight, J. L. and McIlwraith, C. W. Early events in cartilage repair after subchondral bone microfracture. *Clin Orthop Relat Res*, 2003. 407 215-227; Frisbie, D. D., Trotter, G. W., Powers, B. E., Rodkey, W. G., Steadman, J. R., Howard, R. D., Park, R. D. and McIlwraith, C. W. Arthroscopic subchondral bone plate microfracture technique augments healing of large chondral defects in the radial carpal bone and medial femoral condyle of horses. *Vet Surg*, 1999. 28(4): 242-255; Miller, B. S., Steadman, J. R., Briggs, K. K., Rodrigo, J. J. and Rodkey, W. G. Patient satisfaction and outcome after microfracture of the degenerative knee. *J Knee Surg*, 2004. 17(1): 13-17. Steadman, J. R., Miller, B. S., Karas, S. G., Schlegel, T. F., Briggs, K. K. and Hawkins, R. J. The microfracture technique in the treatment of full-thickness chondral lesions of the knee in National Football League players. *J Knee Surg*, 2003. 16(2): 83-86; Steadman, J. R., Briggs, K. K., Rodrigo, J. J., Kocher, M. S., Gill, T. J. and Rodkey, W. G. Outcomes of microfracture for traumatic chondral defects of the knee: average 11-year follow-up. *Arthroscopy*, 2003. 19(5): 477-484].

Two other methods for cartilage repair are used currently but not extensively as neither gives fully satisfactory results. Specifically, in Osteochondral Autogenous Transplant System (OATS), autogenous osteochondral plugs are harvested from a donor site with sound cartilage and transplanted to the recipient site(s) of the defect(s) [Hangody, L., Feczko, P., Bartha, L., Bodo, G. and Kish, G. Mosaicplasty for the treatment of articular defects of the knee and ankle *Clin Orthop Relat Res*, 2001. 391: (S) 328-336; Bobic, V. Autologous osteo-chondral grafts in the management of articular cartilage lesions. *Orthopade*, 1999. 28(1): 19-25]. This procedure is difficult, invasive and can only be applied in a limited way since it creates as many damaged sites as those intended for repair. Further, it takes some 60 to 90 minutes to complete.

The other repair method, which uses Autogenous Chondrocytes Implants (ACI), is completed in two surgical procedures [Peterson, L., Minas, T., Brittberg, M. and Lindahl, A. Treatment of osteochondritis dissecans of the knee with autologous chondrocyte transplantation: Results at two to ten years. *J Bone Joint Surg Am*, 2003. 85(S1): 17-24; Brittberg, M., Lindahl, A., Nilsson, A., Ohlsson, C., Isaksson, O. and Peterson, L. Treatment of deep cartilage defects in the knee with autologous chondrocyte transplantation. *N Engl J Med*, 1994. 331(14): 889-895].

In the first procedure, some of the patient's sound cartilage is harvested, from which the chondrocytes are isolated and expanded over a period of six weeks, after which, in a second operative procedure, they are injected back into the site of the defect. Amongst the disadvantages of the ACI treatment are: (a) the quality of the tissue resulting from this surgical intervention is dubious; (b) the procedure requires an undesirably long rehabilitation period, during which weight bearing is severely restricted with consequent muscular atrophy; (c) frequently ectopic formation of cartilage is observed, the removal of which requires a further surgical procedure; (d) the treatment is completed in two surgical procedures, the second of which can take about 2 hours; (e) the treatment costs in total is affordable by a few. Other emerging treatment (but not yet in wide use) is the one developed by Hollander and colleagues [Hollander A P, Dickinson S C, Sims T J, Brun P, Cortivo R, Kon E, Marcacci M, Zanasi S, Borrione A, De Luca C, Pavesio A, Soranzo C, Abatangelo G: Maturation of tissue engineered cartilage implanted in injured and osteoarthritic human knees. *Tissue Eng* 2006, 12:1787-1798], a cell based treatment, in which Chondrocytes were isolated from healthy cartilage removed at arthroscopy (presumably from the recipient). The cells were cultured for 14 days, seeded onto esterified hyaluronic acid scaffolds (Hyalograft C), and grown for a further 14 days before implantation.

Moreover, a method and apparatus for the repair of damaged cartilage is disclosed in WO 01/39694. The repair method comprises forming a narrow groove around the damaged cartilage site with the groove extending into the bone tissue underlying the cartilage. The damaged cartilage is first removed and a biocompatible fibre based replacement material is positioned at the as-formed defect site (which, being intended for repair, will interchangeably be referred to as the repair site). This replacement material is anchored in position at the bone using a retaining means in the form of a sheet-like fibrous material that either extends from (or is positioned over) the replacement material prosthetic and extends into the groove to the underlying bone. Accordingly, the replacement material is anchored in position initially by the frictional contact of the sheet-like retaining means that is wedged and crumbled within the groove. A second stage biological fixation then occurs as tissue grows into the retaining means within the groove to replace the initial mechanical anchorage.

However, in vivo preclinical trials have shown that the retaining sheet described above did not consistently retain the pad and in a number of cases moved so that the pad was dislodged from the repair site. Further, in the trials the integration of the ingrown repair tissue with the surrounding native cartilage was poor/inconsistent, and this was attributed to the presence of the outer anchorage sheet that retained the implant scaffold/pad at the repair site. Also, whilst this sheet is not of an impervious structure, it is believed that its porosity was not sufficient to allow osseous tissue ingrowth within the groove. The interposition of the anchorage sheet between the scaffold and the native cartilage and bone surrounding the defect site may have impeded migration of the repair tissue across the sheet thereby compromising the lateral integration of the implant. The partial success of these existing, known devices highlighted the need for apparatus and methods to repair damaged cartilage sites that exhibit consistently effective and patent anchorage at the repair site and maybe more conveniently implanted during any one surgical procedure, taking into account, and addressing the different demands, placed by the size, shape, and accessibility of the different potential repair sites.

SUMMARY

Accordingly, the inventors provide a prosthetic implant in which a fibrous material is shaped and dimensioned so as to occupy a defect site from which damaged cartilage tissue has been removed with the intent of repairing it. The fibrous material is held securely in position at the repair site with a retaining element in the form of projecting flexible strips or legs for anchoring the fibrous materials that may be conveniently introduced into a groove formed around or adjacent to the perimeter of the repair site. Initial mechanical anchorage is provided by the frictional contact between the retaining element and the inner walls of the groove. Secondary biological fixation then augments/enhances the initial mechanical anchorage as tissue grows into the retaining element scaffold material (and the pad material at the defect site) following implantation. Importantly, the anchorage element of the present invention is integrated with the scaffold pad by a unifying procedure that leaves the pad readily accessible for tissue ingrowth from the lateral direction. This has been found to provide complete biological fixation and enhanced strength of repair.

According to a first aspect of the present invention there is provided an implantable prosthetic device for the repair of damaged connective tissue in an animal or a human being, said device comprising: a biocompatible pad having an open structure formed from entangled fibres to provide a scaffold for the in-growth of tissue into the pad which is shaped and dimensioned to occupy a site from which damaged connective tissue has been removed; a woven or non-woven textile anchor having an open structure to provide a scaffold for the in-growth of tissue into the anchor; wherein the pad and anchor are connected together and integrated to form a unitary structure by entanglement of the fibres of the pad and the fibres of the anchor; wherein the anchor comprises woven or non-woven textile legs that extend away from a perimeter region of the pad, each leg having longitudinal edges and spaced apart relative to one another along their respective lengths such that in an unfolded orientation the longitudinal edges of neighbouring legs are not in contact with one another.

Preferably, the textile legs are formed integrally with the main body of the anchor that is connected to the pad by entanglement of the fibres so as to be regarded an extension of the main body. Alternatively, the textile legs or strips may be attached to the main body.

Optionally, the replacement material is in the form of at least one circular pad. It will be apparent to one skilled in the art that the thickness of replacement pads used will be determined by the depth of the resultant recess formed after removal of damaged tissue.

It will also be apparent to one skilled in the art that replacement material is broadly construed as materials which facilitate repair such as, tissue (eg cartilage, bone, synovium), cells from different origins including chondrocytes, biocompatible gel, comprising tissue/cells, synthetic bone material or coral. Such materials, where possible, are formed as a fibrous material and in particular a collection or consolidation of randomly arranged fibres. Alternatively or in addition, these materials that facilitate repair may be incorporated into a fibrous scaffold by seeding a fibrous scaffold formed from a first material with a second material configured to facilitate tissue ingrowth into the repair site. The material may be bioabsorbable or non-bioabsorbable. More preferably still the pad provides an increased surface area to which cells adhere and proliferate. More preferably still the pad promotes the differentiation of cells which adhere thereto.

Preferably said pad is adapted to provide a cell culture surface to which at least one of the following cell types adhere, proliferate and/or differentiate: chondrocytic progenitor cells (stem cells); chondrocytes or cartilage-forming cells. Furthermore cells can be genetically engineered to express gene products which, for example facilitate the attachment and/or differentiation of cells which infiltrate the pad. Preferably the pad is immune silent. It will be apparent to one skilled in the art that it is desirable that the pad does not provoke an immune reaction in the patient.

In conditions where extensive damage to tissue has occurred it is preferable to use a plurality of closely associated pads. For example, a first circular pad may be positioned within a first groove at a site to be repaired. A second groove of a lager diameter may then be concentrically formed around the first groove and a second, ring/donut shaped pad, may be positioned within the second concentric groove. In this arrangement, two retaining means are used to anchor the circular pads of replacement material at the site to be repaired. The width of the anchoring leg/strip in the case of a single circular pad should be less than a quarter of the pad's circumference so that when introduced in the groove surrounding the damaged site intended for repair, the anchorage legs/strips do not overlap thus presenting a denser structure and hence less permeable one for tissue ingrowth. Where a circular pad is implanted concentrically with a ring/donut-shaped pad, the width of the anchoring strips in both pads must be of a size that can be accommodated within the grooves without overlapping. The positions of the legs/strips in both of the above pads can be staggered so that a leg from one pad can alternate with an adjacent leg from the other pad in the common groove.

Circular pads used singly or in conjunction with a concentric ring-shaped pad would be appropriate/suitable where the defect site is conveniently of a near circular shape, and of a diameter of no more than 12 mm for repair achieving the with single pad of substantially the same diameter, or where the defect is approximately 22 mm in diameter the repair of which can be achieved with two concentric pads as described above.

Apart from the above mentioned size and shape constraints on the use of the circular configurations of the repair constructs there is another constraint; that of requirement that the common axis of the concentric grooves be substantially normal to the surface of the repair site. If the deviation of the grooves common axis from normal is substantial, the circular pads would not fit the repair site, which will be elliptical rather than circular as a result of the inclination of the groove axis to the surface of the repair site.

Additionally, some of defect sites are not accessible for forming a groove with its axis directed perpendicular to the defect site—for example areas on the tibial condyles. To address this problem the present invention discloses alternative designs that allow the following: (a) repairs to be made of damage sites of different shapes and of different or of larger dimensions than those that are suitable for repair with circular pads, and (b) to allow anchorage in grooves that are cut at in a direction that is not perpendicular to the surface of the damaged site.

Polygonal pads, in particular square or rectangular pads, with integral similar anchoring means as described above, whereby the legs/strips are jutting from the pad at or near the four edges, can be used to repair a damaged site that has substantially a square or rectangular geometry, and in addition where the damaged site is in a location on the joint that does not permit making grooves that are perpendicular to the surface of the damaged site. Grooves can be made each independently and in a direction as the access to the damage site may permit. Square or rectangular pads as described may be positioned side-by-side so that certain edges of the pad are in contact with neighbouring pads to form a pad assembly at the repair site. In this configuration, the legs of the anchor, of neighbouring pads, are positioned within common grooves and this may be conveniently achieved using a simple blade-like pusher, tool or device. Preferably, three or four square or rectangular pads are positioned together such that the assembly forms a larger square or rectangle in plan view. The purpose of such arrangements is to enable repairing larger defects.

A further embodiment is a larger pad of multiple the dimension of the a square pad, with anchor strips jutting from it around its edges and from its main body to substantially uniformly distribute the anchoring sites of a larger pad, and such that the pad can be cut during surgery to size that substantially matches that of the defect, and in the process those unnecessary anchoring strips are trimmed off the pad, so that it conveniently suits a repair site.

Preferably the retaining anchor, including the integrally formed legs/strips, is in the form of a thin, flexible mesh, more preferably made of a woven fabric. Preferably, the anchor material comprises pores or holes in the material to facilitate tissue in-growth. Where the anchor is woven, an open weave is created preferably with three groups of weft yarn and three groups of warp yarn with each warp and weft of the group of three being interwoven independently or individually with each perpendicular yarn (weft or warp).

Alternatively, the retaining means is made of non-woven fabric. However, the non-woven fabric comprises the open structure to facilitate tissue in-growth and may comprise the same material as the pad formed from entangled randomly arranged fibres being a felt-like material.

The entanglement of the pad and textile anchor is achieved with a process of needling which comprises oscillating a needle or thin rod-like member back and forth into the pad and anchor so as to push and pull the fibres of the pad and anchor in the same forward and reverse directions, perpendicular to the plane of the strip-like anchor to create entanglement. Prior to needling, the pad is positioned at one side of the central region of the substantially planar anchor and following the needle process, a percentage of the pad fibres are displaced through the anchor and extend beyond the alternate opposed surface of the central region of the anchor. Accordingly, when the needling process is complete up to approximately half of the pad fibres extend (in the perpendicular direction) from both sides of the central region of the planar anchor. Alternatively, 40%, 30%, 20% or 10% of the pad fibres may be needled to extend from the opposite face of the anchor from which the pad was first positioned before needling.

When making a groove into the bone for the purpose of anchoring a device such as described, optionally, the at least one groove can be made with a knife, a scalpel or straight or curved punch or with an oscillating saw. It will be apparent to one skilled in the art that the use of an oscillating saw enables the surgeon to make individual geometric cuts around the damaged tissue thus minimising the damage to healthy tissue. For example, and not by way of limitation, the surgeon can make a series of straight cuts around a damaged area to surround the damaged tissue. Typically, this results in damaged area being enclosed by a polygonal series of cuts. Where a larger pad has further anchoring strips within its main body (beside those around its edges) the additional grooves within the repair site should be made to provide further anchor for the pad.

Optionally, the means for forming the narrow groove is a cylindrical reaming device as described in WO 01/039694.

Preferably the depth of the groove is a multiple of the thickness of tissue which is replaced. It will be apparent to one skilled in the art that the groove is of sufficient depth to securely retain the replacement material so that it does not get dislodged as the joint articulates. Optionally, the groove depth is greater than the distance across the pad. Preferably, the length by which each leg extends away from the perimeter of the pad is equal to or greater than the distance across the pad (diameter). Optionally, the depth of the groove is at least two, three or four times that of the thickness of the cartilage which is replaced. Accordingly, the groove depth is at least equal to the length of each leg of the anchoring means. The deeper the groove the more secure the implanted replacement material. However care must be taken to ensure the groove is not too deep since this would represent increased invasiveness.

Typically, the damaged tissue can be excised using a scraping device. Alternatively, the damaged tissue is removed using a wire brush. Preferably the wire brush is provided with guide means to restrict the abrasive action of the brush to the area of damaged tissue.

In situations where a scraping device is used to remove damaged cartilage, it is advantageous to use guard means to prevent the scraping device damaging surrounding healthy cartilage. Typically, a guard means is located in the groove to abut the scraping device during removal of the damaged cartilage. A guard means is manufactured from any robust, tensile materials to confer protection (eg steel, high density plastics).

Preferably a tubular device is used for pushing the retaining anchor into a circular groove. Alternatively, if the groove is polygonal in form the pushing device is suitably adapted to facilitate introduction and securing of the anchor in the groove. For example, such pushing device can be a straight-edged blade.

Preferably, each leg of the anchor when inserted into the groove does not fold and crease over neighbouring legs inserted into the groove.

According to a second aspect of the present invention there is provided a method of manufacturing an implantable prosthetic device for the repair of damaged connective tissue in an animal or a human being, the method comprising: providing a biocompatible pad having an open structure formed from entangled fibres to provide a scaffold for the in-growth of tissue into the pad which is shaped and dimensioned to occupy a site from which damaged connective tissue has been removed; connecting a woven or non-woven textile anchor having an open structure to provide a scaffold for the in-growth of tissue into the anchor to the biocompatible pad to form an integrated unitary structure by entangling the fibres of the pad with the fibres of the anchor; wherein the anchor comprises woven or non-woven textile legs that extend away from a perimeter region of the pad, each leg having longitudinal edges and spaced apart relative to one another along their respective lengths such that in an unfolded orientation the longitudinal edges of neighbouring legs are not in contact with one another.

According to a third aspect of the present invention there is provided an implantable prosthetic device for the repair of damaged connective tissue in an animal or a human being, said device comprising: a biocompatible pad having an open structure formed from entangled fibres to provide a scaffold for the in-growth of tissue into the pad which is shaped and dimensioned to bridge or connect connective tissue; a woven or non-woven textile reinforcement element having an open structure to provide a scaffold for the in-growth of tissue into the element; wherein the pad and element are connected together and integrated to form a unitary structure by entanglement of the fibres of the pad and the fibres of the element.

Preferably, the reinforcement element is formed as a strip. More preferably, the reinforcement element is integrated with the pad at a perimeter region of the pad. More preferably, the reinforcement strips extends around the entire perimeter of the pad at its edge. Preferably, the pad is circular or polygonal.

Preferably, the prosthetic device comprises reinforcement element strips extending across the body of the pad between its perimeter. The device may comprise one or a plurality of reinforcement strips extending across the pad between respective edges.

The reinforcement elements are configured to receive sutures or other medical cords to attach the device to connective tissue such as a torn rotator cuff and relevant surrounding tissue/muscles. The textile strips that are unified by entanglement of the respective fibres of the pad and strips prevent the pad being torn by the connective sutures or medical cords which otherwise occur with existing bridging or connective devices following surgery.

BRIEF DESCRIPTION OF THE DRAWINGS

A specific implementation of the present invention will now be described, by way of example only and with reference to the accompanying drawings in which.

DETAILED DESCRIPTION

Figure 1:
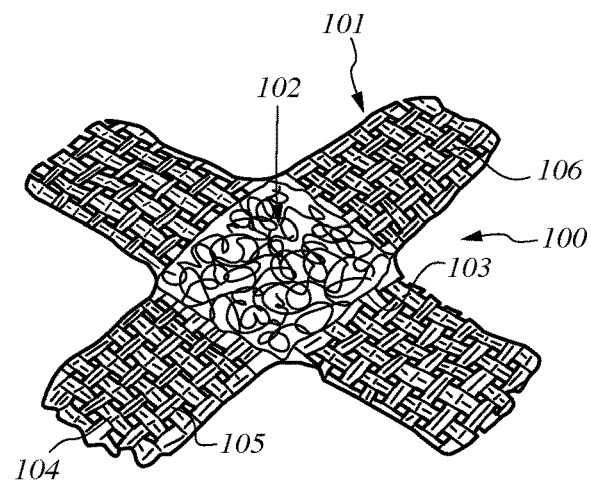
FIG. 1 is a perspective view of a prosthetic pad and anchor according to a preferred embodiment of the present invention.
Figure 2:
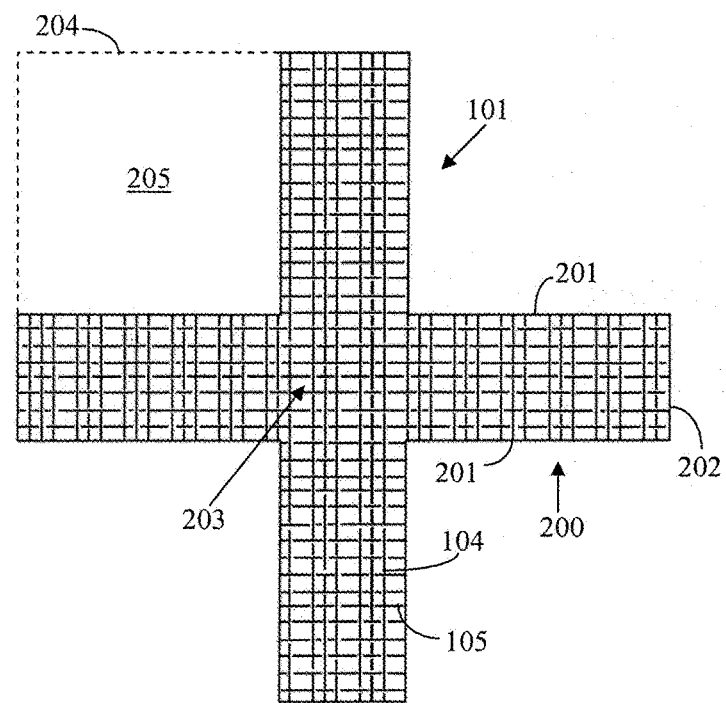
FIG. 2 is a plan view of the anchor means of FIG. 1.
Figure 3:
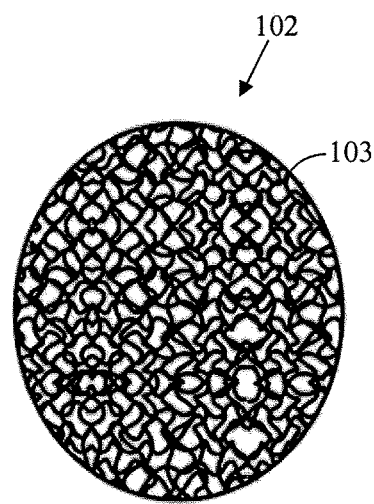
FIG. 3 is a plan view of the prosthetic pad of FIG. 1.

Referring to FIG. 1 the implantable device 100 comprises a woven sheet-like anchor 101 connected to a non-woven felt like pad 102 formed from entangled fibres to create a fluffy or wispy material that is positioned centrally at anchor 101. Sections of the anchor 101 comprise a mockleno or trueleno weave in which three substantially parallel alighted warps 104 are interwoven individually and independently with three substantially parallel aligned wefts 105 to from a porous structure in which pores or holes 106 are created between the perpendicular aligned and interwoven wefts and warps. Holes 106 are configured to facilitate tissue in growth when prosthetic 100 is implanted in vivo.

Referring to FIGS. 1 to 6, the sheet like anchor 101 may be formed from a single woven sheet 204 from which square or rectangular sections 205 are removed (cut away) to create a substantially planar sheet-like having a cross form with four rectangular strips or legs 200 that extend from a central portion 203. Each planar leg 200 comprises two opposed longitudinal 'length' edges 201. An end 'width' edge 202 connects length edges 201 at a region furthest from central section 203. Each anchor strip 101 comprises warps 104 interwoven with wefts 105 that are aligned respectively parallel in each leg section 200 and central section 203.

The non-woven pad 102 is positioned over central section 203 of anchor 101 such that each leg 200 extends from a perimeter 103 region of the pad 102. In the unfolded orientation of FIGS. 1, 2 and 4, each leg 200 of the quadrant is separated from each neighbouring leg to create a gap region between opposed length edges 201. According to the preferred embodiment, each leg 200 comprises a width that is slightly less than one quarter of the circumference of the disc or dome shaped pad 102. Additionally, the length of each leg 200 from the end edge 202 to the pad perimeter 103 is approximately equal to a diameter (or width) of pad 102.

Figure 6:
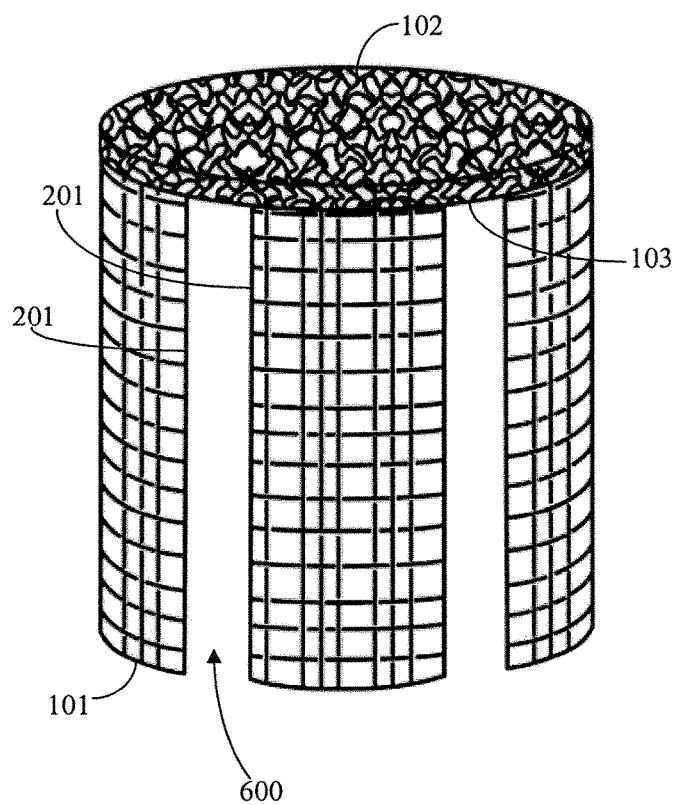
FIG. 6 is a perspective view of the prosthetic device of FIG. 5 with the retaining anchor bent in a configuration it will have after implantation, with the four strips/legs being retained within a groove encircling the defect site also illustrated in FIG. 8.

FIG. 6 illustrates prosthetic 100 orientated when it has been implanted with the anchoring strips 200, folded or bent at the region of pad perimeter 103 so as to extend substantially perpendicular to the plane of pad 102. In this orientation, each leg or flange 200 is separated from each neighbouring leg 200 by a gap region 600, and so avoids any overlap of the anchorage material 101 in the deeper regions of the anchor groove which may otherwise prevent tissue and bone ingrowth and inhibit secondary biological fixation and repair of the defect site. Significant folding and creasing of each leg 200 also makes it difficult for a surgeon to implant satisfactorily to ensure optimised initial mechanical anchorage within the groove.

Figure 4:
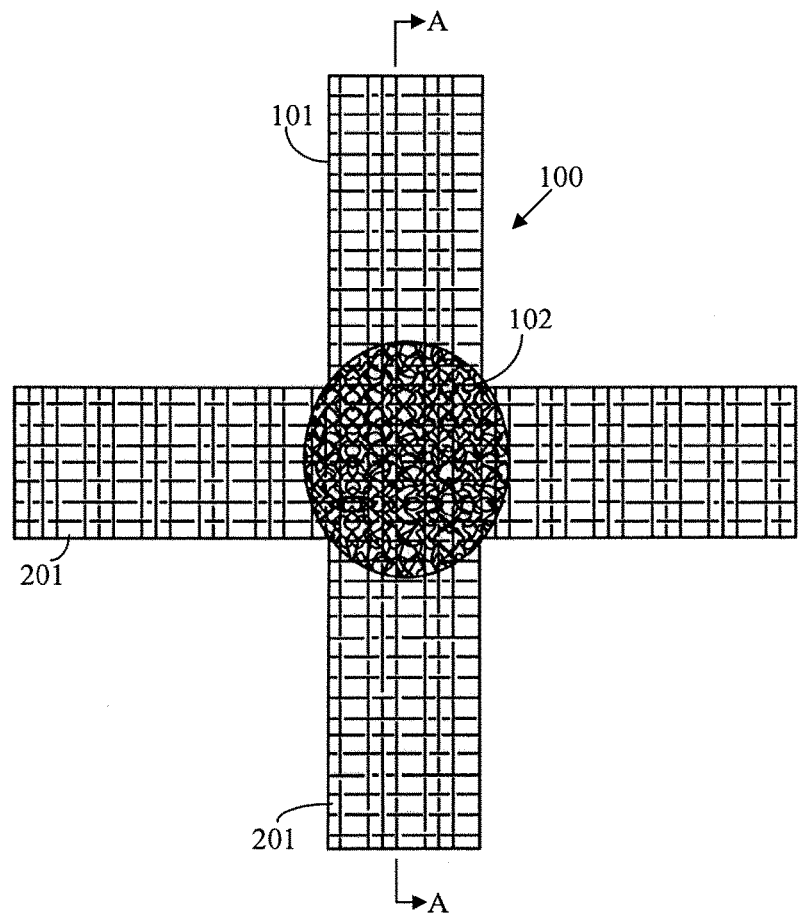
FIG. 4 is a plan view of the pad and anchor assembly of FIG. 1.
Figure 5:
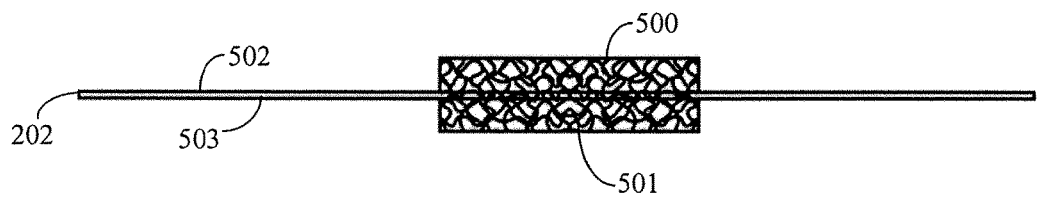
FIG. 5 is a cross sectional elevation view of the prosthetic device of FIG. 4.
Figure 7:
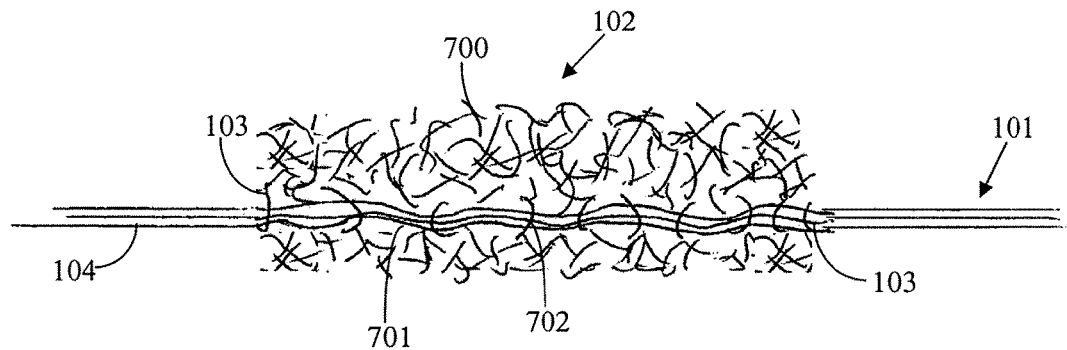
FIG. 7 is a further cross sectional view of the prosthetic device of FIG. 5.

FIGS. 5 and 7 illustrate a cross section through A-A of FIG. 4. Via a process of 'needling' the fibres 700 of pad 103 are intertwined and mixed with the fibres 104, 105 of anchor 101 so as to create an entanglement region 701, 702 within the pad perimeter 103. Successive needling of the central region 203 defused pad fibres 700 through the woven anchor 101 such that pad 103 comprises an 'upper' region 500 extending perpendicular from an upper facing surface 502 of anchor 101 and an opposed 'lower' region 502 extending perpendicular from a opposed downward facing surface 503 of planer anchor 101. By adjusting the duration of the needling process, the relative ratio of 'upper' region 500 and 'lower' region 501 may be adjusted as appropriate.

Figure 8:
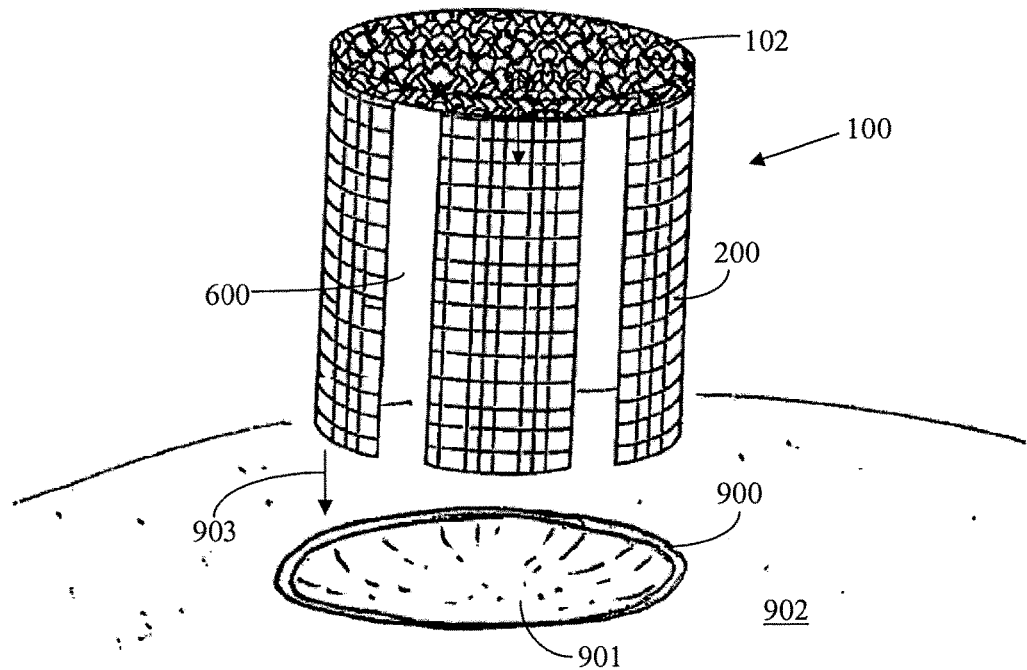
FIG. 8 illustrates the prosthetic of FIG. 6 lowered into position at an anchoring groove according to one method of implantation.

FIG. 8 illustrates implant 100 with the anchoring strips legs 200 folded at the region of pad perimeter 103 ready for insertion within a narrow cylindrical groove 900 formed at the perimeter of a cavity 901 from which damaged cartilage has been removed from a cartilage site 902. As legs 200 are spatially separated along their length by gap region 600, they may be conveniently inserted within groove 900 making it easy for a surgeon to position pad 102 appropriately at cavity 901.

Figure 9:
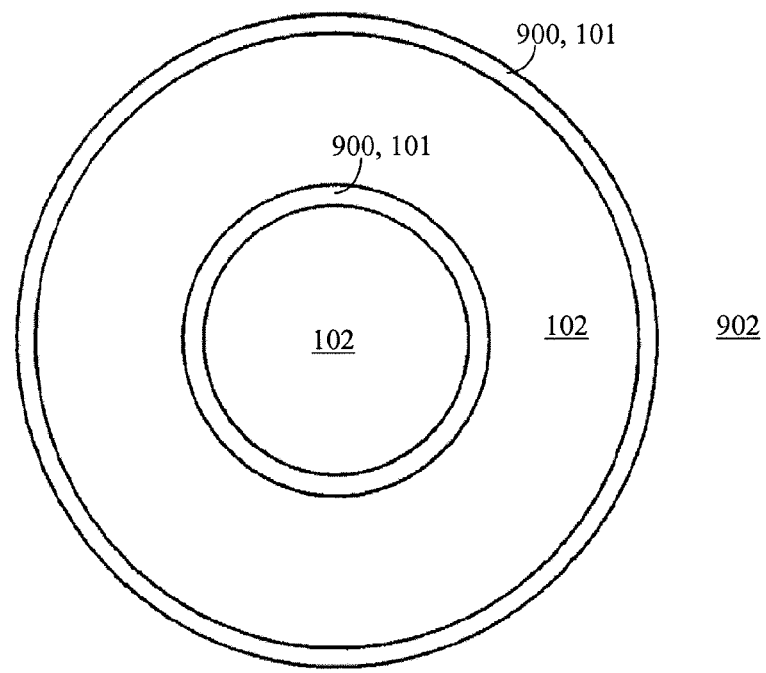
FIG. 9 is a plan view of cartilage repair using another embodiment of the present invention.
Figure 10:
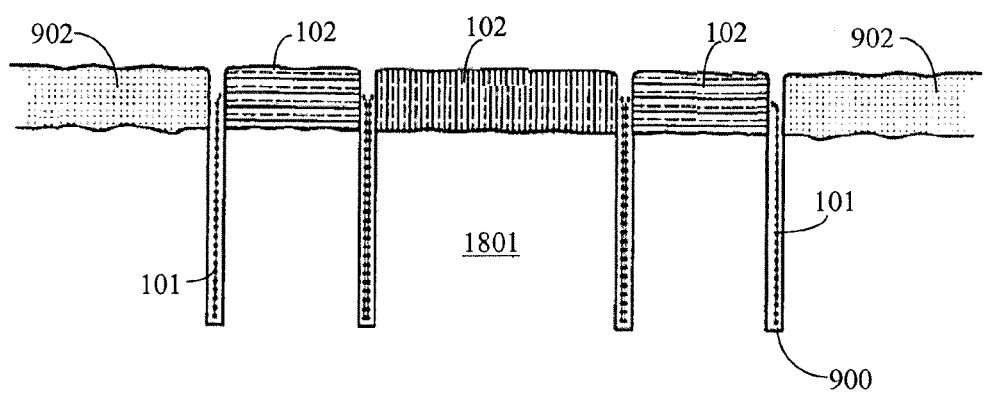
FIG. 10 is a cross sectional side view of the repair method of FIG. 9 to repair a larger damaged region.

FIG. 9 illustrates repair of a large damaged site of substantially circular geometry, with two concentric pads 102, one circular, the other in the form of a ring or donut. The anchoring strips share the smaller groove 900, but the anchoring strips of the two pads are of such dimensions and are juxtaposed in such a manner that they do not overlap within the groove. The donut is like pad is also anchored in the outer groove 900. FIG. 10 is a section through the centre of FIG. 9.

Figure 11:
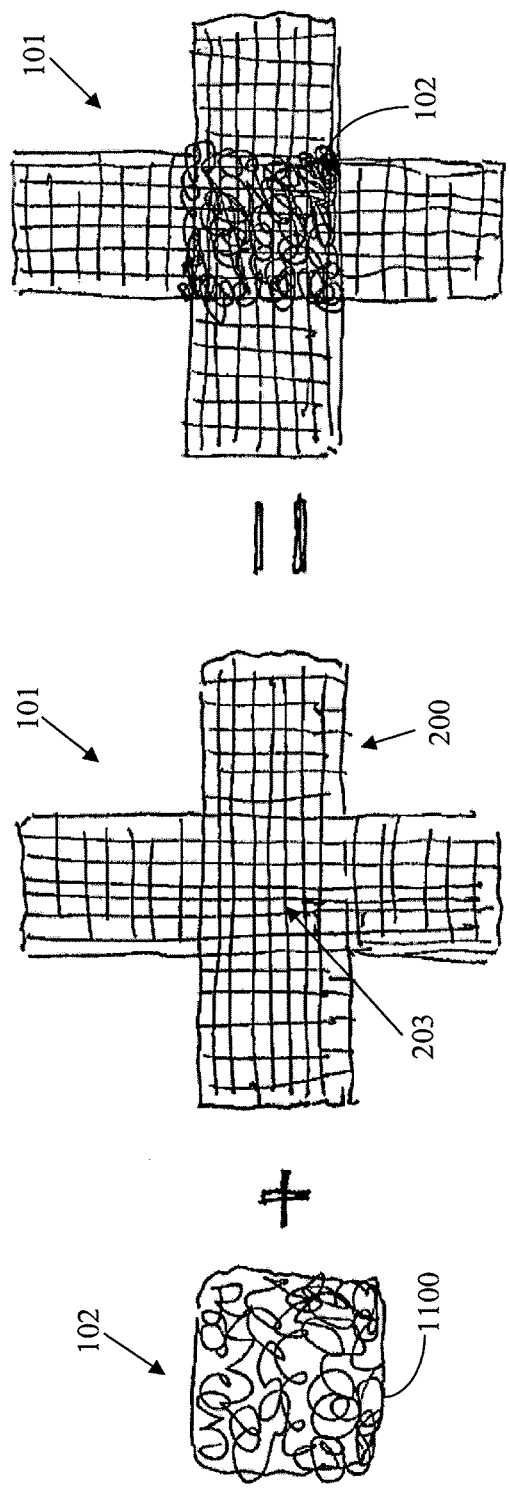
FIG. 11 illustrates a square repair pad with a cross like anchoring means as previously shown, according to a further embodiment.

FIG. 11 illustrates a further specific implementation of the present device in which a square pad 102 is attached to the cross-shaped textile anchor 101 as described with reference to FIGS. 1 to 7. According to the further embodiment, the square pad 102 comprises perimeter edges 1100 that defines central portion 203 of anchor 101 when pad 102 and the anchor are unified and secured together by a needling process as described. That is, each leg or strip 200 extends away from the pad edge 1100.

Figure 12:
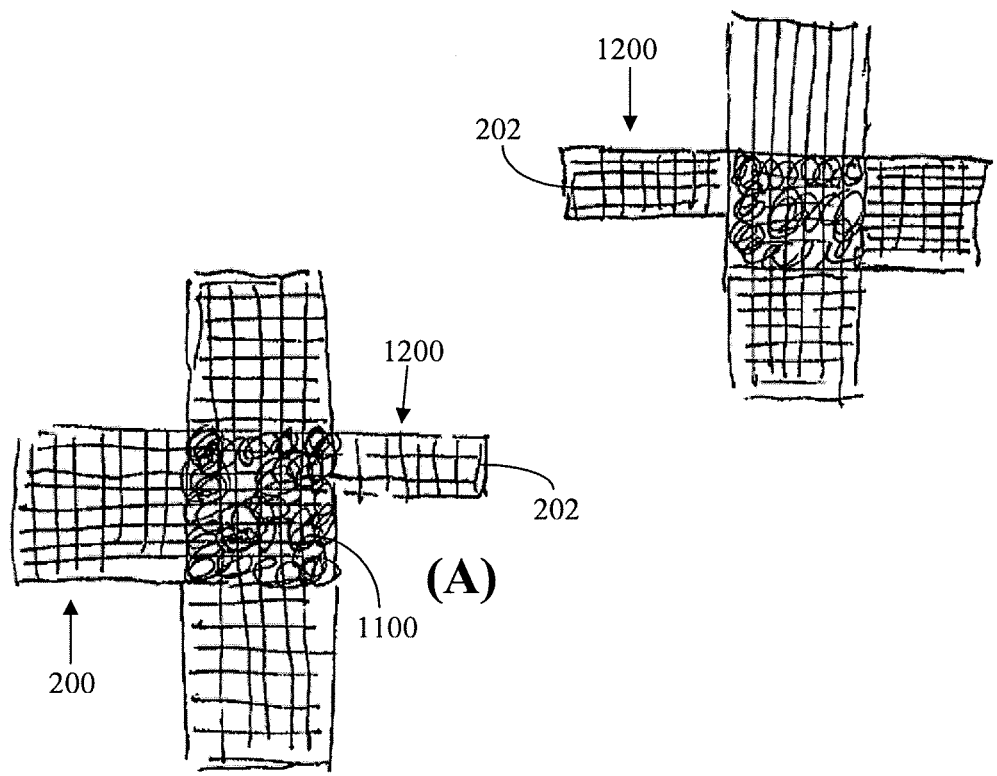
FIG. 12 (A-B) illustrates two square repair pads for repair of a rectangular defect, where the anchoring strips sharing a common groove have been trimmed so that they do not overlap in the groove; The two pads can be of different sizes to suit the shape and size of the defect site.
Figure 12:
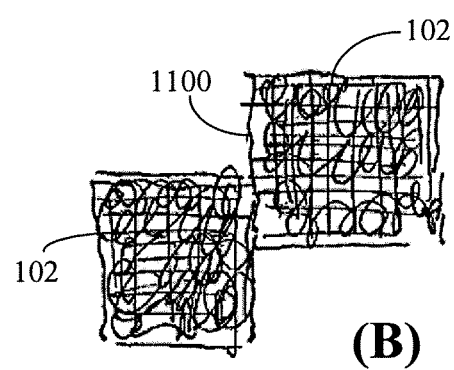

FIGS. 12(a) and (b) illustrate a variation of the embodiment of FIG. 11 in which one anchorage strip 1200 comprises a reduced width having a width edge 202 that is approximately half that of the remaining three legs/strips 200. That is, strip 1200 extends approximately half the distance along pad edge 1100 and comprises a substantially uniform width along its length to outermost edge 202. Referring to FIG. 12(B), the devices of FIG. 12(A) are configured to be positioned side-by-side but in a staggered or off-set alignment so which that half the length of each edge 1100 of the two neighbouring pads 102 are in contact with one another. In this anchorage position, strips 1200 are configured to share a common groove, but do not overlap within the groove.

The devices of FIGS. 11 and 12(A) and (B) may be anchored in position at a defect site using linear grooves formed for example using an oscillating saw or other linear blade punch or cutting device.

Figure 13:
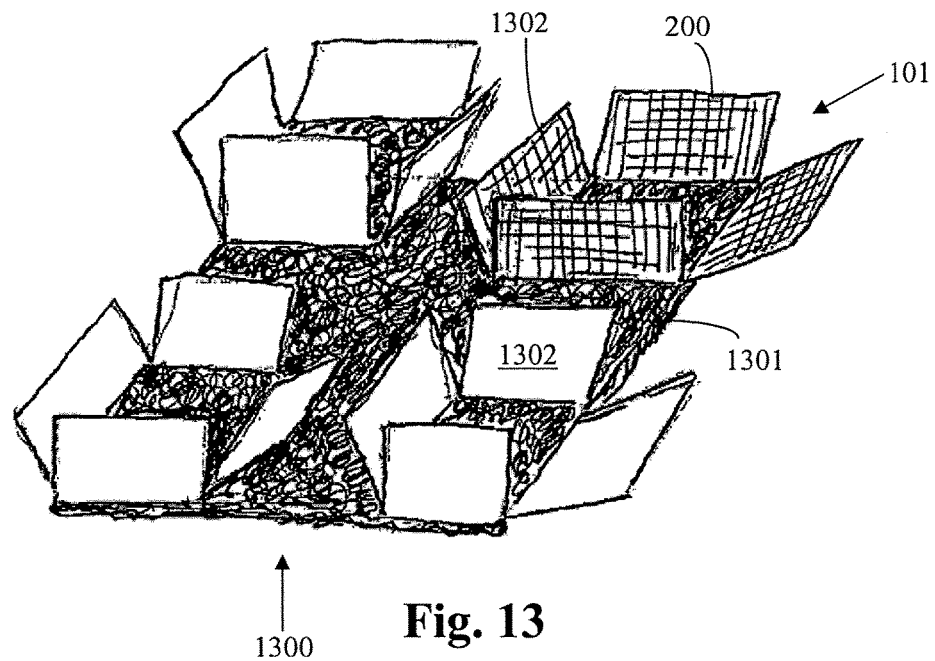
FIG. 13 illustrates a large repair pad/patch with rows of cross-like anchoring means integrated with the structure of the pad, according to further embodiment.

FIG. 13 illustrates a further embodiment of the present implantable device to repair respectively larger defect sites. The implant comprises a pad 1300 of the same material as the device of FIGS. 1 to 12 having a rectangular shape defined by perimeter edges 1301 according to the specific embodiment. A plurality of fabric anchors 101 are connected and integrated with pad 1300 using the same needling and fibre entanglement process as described. As the length and width of the pad 1300 is greater than the width 202 of each central portion 203, each central portion 203 when connected to the pad 300 sits within the perimeter of pad edges 1301. According to the embodiment of FIG. 13, the pad 1300 is sized to accommodate four anchorage regions 101 with each central portion 201 positioned towards each of the four corners of the rectangular pad 1300. Accordingly, two legs of each anchor 200 extend from the perimeter edge 1301 of pad 1300. Additionally, the remaining two legs 1302 extend from an underside surface of pad 1300 within perimeter region 1301. Importantly the size and shape of the implantable device having pad 1300 and anchorage regions 101 may be determined by a surgeon simply cutting pad 1300 between anchorage regions 101. Of course it is also possible to trim or remove selectively legs 200, 1302 prior to implantation at a specific location depending upon, for example, access to the repair site and the ease of groove formation. According to further embodiments, the implant may comprise any number of anchorage regions 101 extending across a sheet of pad material 1300 as rows and columns from which the surgeon may cut the desired size and shape.

Figure 14:
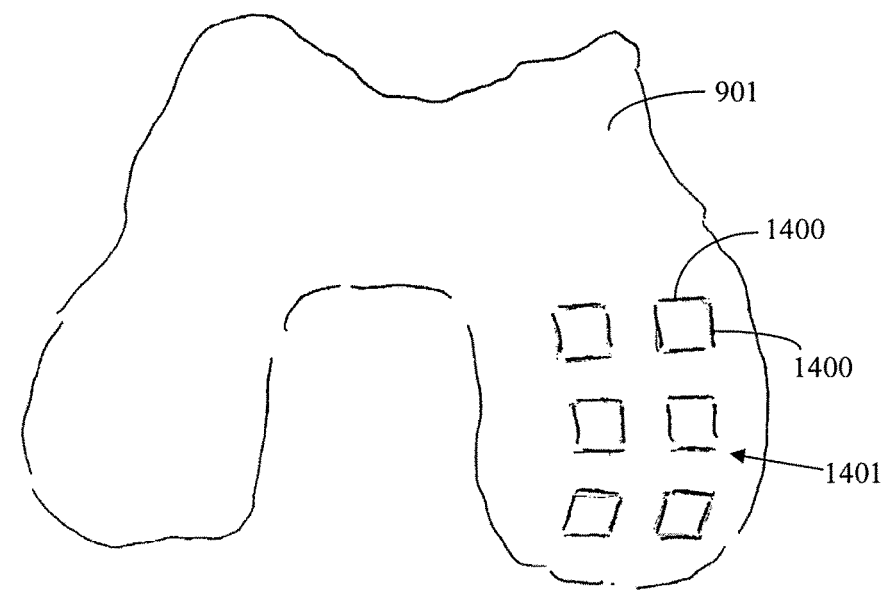
FIG. 14 illustrates the formation of a plurality of straight grooves formed by an oscillating saw, at a knee femoral condyle, to allow the implantation of a repair pad with multiple anchoring strips as shown in FIG. 13.

FIG. 14 illustrates a repair site 901 prepared to receive a form of implantable device similar to that of FIG. 13.

Discreet anchorage zones 1401 are created by forming narrow linear grooves 1400 into the underlying bone to define grooves within an approximate square configuration. Importantly, each individual linear groove 1400 does not necessarily need to intersect with a neighbouring groove 1400 as each anchorage strip 200, 1302 is anchored separately within different respective linear grooves 1400. As illustrated in FIG. 14, an array of the approximately square-shaped anchorage grooves 1401 are created to correspond in size and position to the anchorage strips 200, 1302 extending from pad 1300. Importantly, the linear grooves do not need to be perpendicular to the surface of the bone in the repair site.

Pad 102, 1300 is made of a non-woven fabric of a bioenhancing material which is designed to encourage cell recruitment at a level many times that of untreated material. Pad 102, 1300 may also be bioabsorbable at a rate which is designed to match that of the establishment of a new cartilage layer 902 which is secured to the underlying bone 1801 and the surrounding cartilage 902.

The present synthetic implants are compatible for seeding with cells and/or bio-active substance, to facilitate healing post surgical repair. In particular, the prosthetic material 102, 1300 may be seeded naturally with cells from the joint after the operation. It may be a useful step in the cartilage repair procedure described, to seed the pad 102, 1300 with autologous cells from the patient, for example, chondrocytes, fibroblasts, stem cell progenitor cells of chondrocytes or fibroblasts. The source of these would be the residual cartilage at the defect site 901 which is removed with the rotatory instrument. A fraction of the cartilage residue will be healthy cartilage. On removal of this residue, it is proposed to decimate it further with tissue disrupting devices which are known in the art or any mechanical or chemical means which can effectively release healthy chondrocytes, fibroblasts or stem cells. A non-limiting example of such a device would be a dounce homogeniser.

With the addition of the appropriate medium to the decimated cartilage removed from the repair site, the result would be a cell suspension into which the repair pad can be soaked for a period after which the pad is implanted according to the invention. The tissue disrupting device can be used with alternative tissue such as synovium harvested from the patient and used in the same manner, except that in this case the cells seeding the pad would be synovial fibroblasts instead of chondrocytes.

The advantage of the above is that autologous cells would be used and therefore not rejected by the patient. The use of the pad 102, 1300 ensures that much of the cells remain in the site of repair. It is envisaged that the cells would proliferate resulting in inducing tissue that fills the pad 102, 1300 in a faster manner than if the latter was not seeded. Pad 102, 1300 may also be non-woven fabric of a bioenhancing material, or alternatively can be a piece of tissue, (eg periosteum, synovium. fascia, retinaculum). The anchor 101 may also be a bioabsorbable material, again calculated to be eliminated at a rate compatible with the growth and fixation of the new cartilage to both the bone and the surrounding cartilage.

In the above-described embodiment the pad 102, 1300 is a bioabsorbable material. However in another embodiment the material may be a non-degradable material which is biocompatible and possesses enhanced surface properties so as to attract tissue growth into the material. The prosthetic pad 102, 1300 may have a circular or polygonal geometry of varying thickness so that the prosthetic scaffold chosen may be of a matching thickness to the adjacent cartilage 902. Accordingly the surgeon can select the appropriate pad 102, 1300 to fill an irregular defect.

Figure 15:
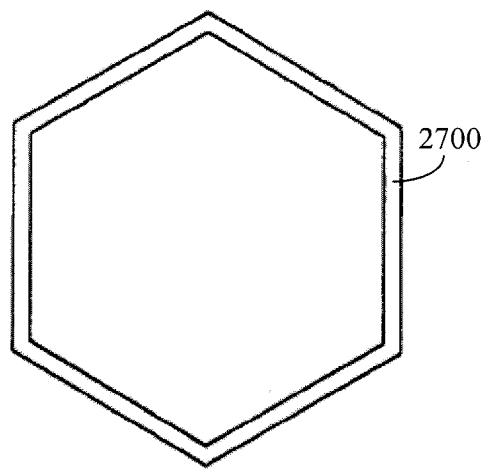
FIG. 15 illustrates the formation of a plurality of straight grooves formed by an oscillating saw to form a polygonal groove encircling a damaged site according to a further embodiment.

The method of implantation of the present devises is disclosed in WO 01/39694 which is incorporated by reference with regard to the repair of damaged cartilage and generally any type of connective tissue. The repair method comprises forming a narrow groove around the damaged tissue site with the groove extending into the bone underlying the tissue. The damaged tissue is first removed and then the implant is positioned at the as-formed defect site. This pad is then anchored in position at the bone using the anchor and in particular the locating of the legs/strips within the as-formed groove(s) to a depth of the underlying bone. The size of the defect size determines the shape, type and size of the repair device that is employed. The present devices may be conveniently cut by a physician from larger pre-formed sheets. For example, a single pad which has an area greater than the whole of the defect area may be used. Alternatively a circular or elliptical pad and an adjacent crescent-shaped pad may be used. The groove illustrated in FIGS. 8 and 9 is circular in form to suit a circular pad. Alternative forms are envisaged for example, FIG. 15 shows a polygonal groove arrangement 2700. It will be apparent that pads 102, 1300 of replacement material are adapted to account for differences in groove arrangements.

An in vivo investigation was undertaken to determine the extent of biological fixation of the implant 100 described with reference to FIGS. 1 to 7.

The purpose of the experiment was to evaluate the cartilage repair device 100 in a preliminary study using adult goats as an experimental model and test safety and efficacy. In the experiment, six adult goats were used. The effectiveness of the implant was then evaluated in three animals two weeks after device implantation and in the remaining three animals six weeks after device implantation. In each animal, two devices 100 were placed, one on the medial femoral condyle of the knee joint and a second one on the lateral femoral condyle of the knee joint. In all animals, the right leg was subjected to surgical intervention.

All devices 100 implanted in the two and six weeks experimental groups retained in situ and were not dislocated nor moved. Most of these devices 100 were put nicely perpendicular to the articular cartilage surface, except in two cases (one in each time group), in which the surgeons had placed it to a somewhat oblique degree to the articular cartilage surface.

The results of the samples of the six weeks group revealed slightly smaller defect sizes with a mean filled defect volume of 86.8% (mean remaining defect volume of 13.2%) compared to a mean filled defect volume of 81.7% (mean remaining defect volume of 18.3%) after two weeks.

Figure 16:
FIG. 16 is a microscopic image of an histologic animal specimen in which the device of FIGS. 1 to 7 has been implanted in the femoral condyle of the knee joint for two weeks.
Figure 17:
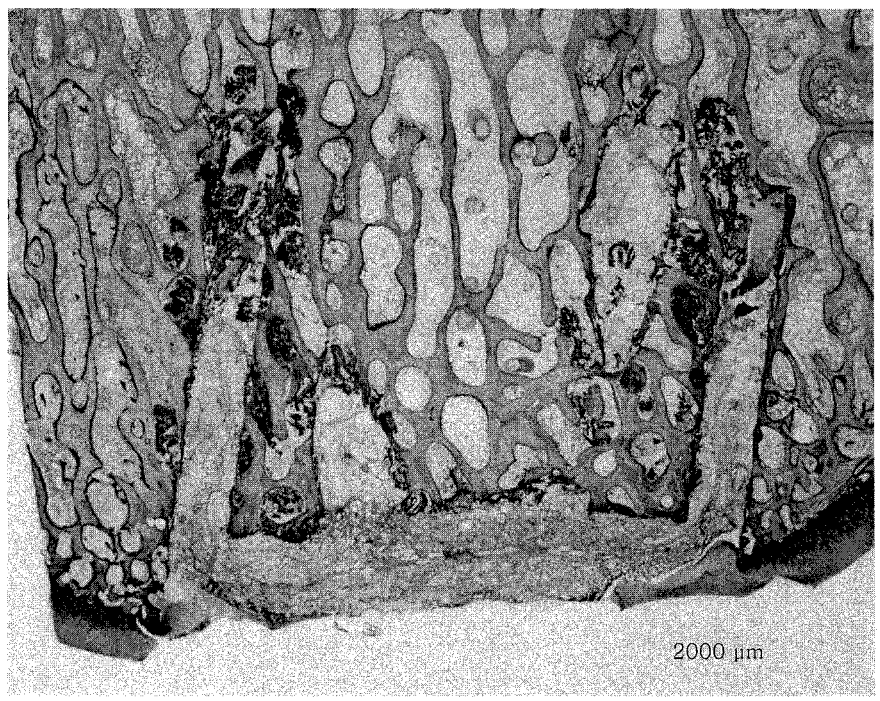
FIG. 17 is a microscopic image of a second histologic animal specimen in which the device of FIGS. 1 to 7 has been implanted in the femoral condyle of the knee joint for two weeks.
Figure 18:
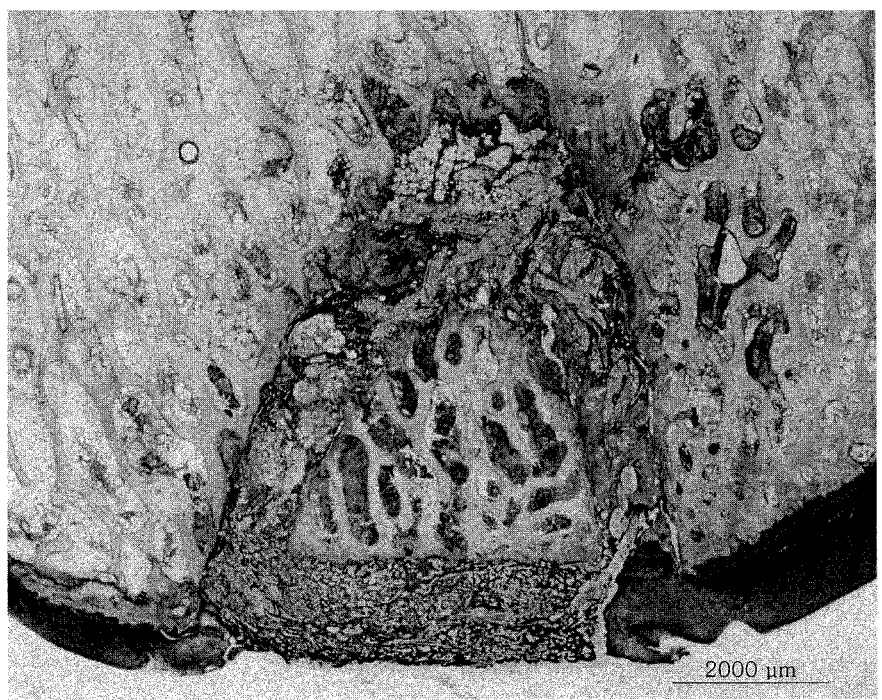
FIG. 18 is a microscopic image of a third histologic animal specimen in which the device of FIGS. 1 to 7 has been implanted in the femoral condyle of the knee joint for two weeks.
Figure 19:
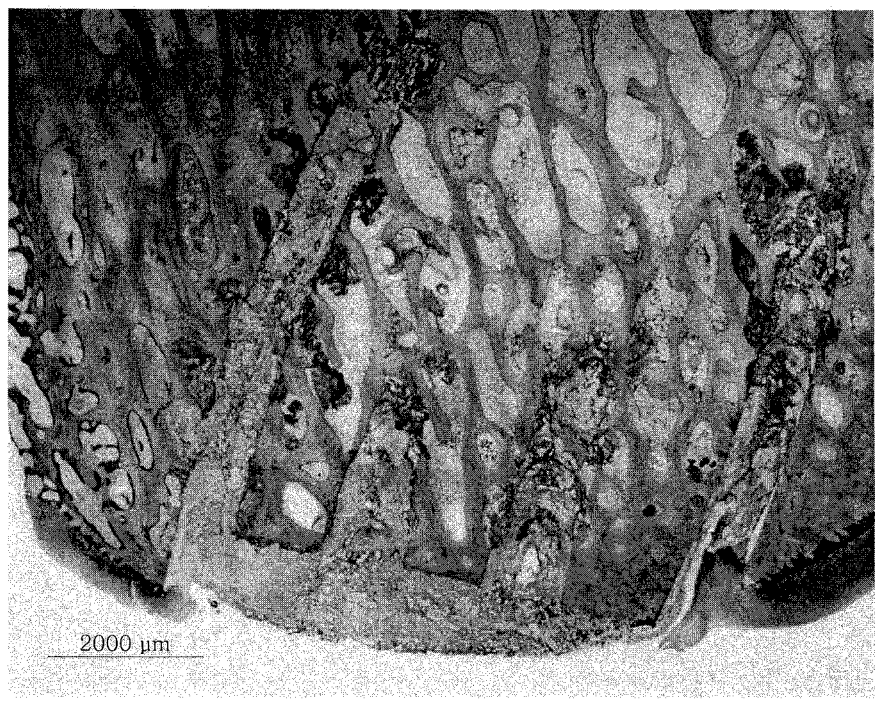
FIG. 19 is a microscopic image of a fourth histologic animal specimen in which the device of FIGS. 1 to 7 has been implanted in the femoral condyle of the knee joint for six weeks.
Figure 20:
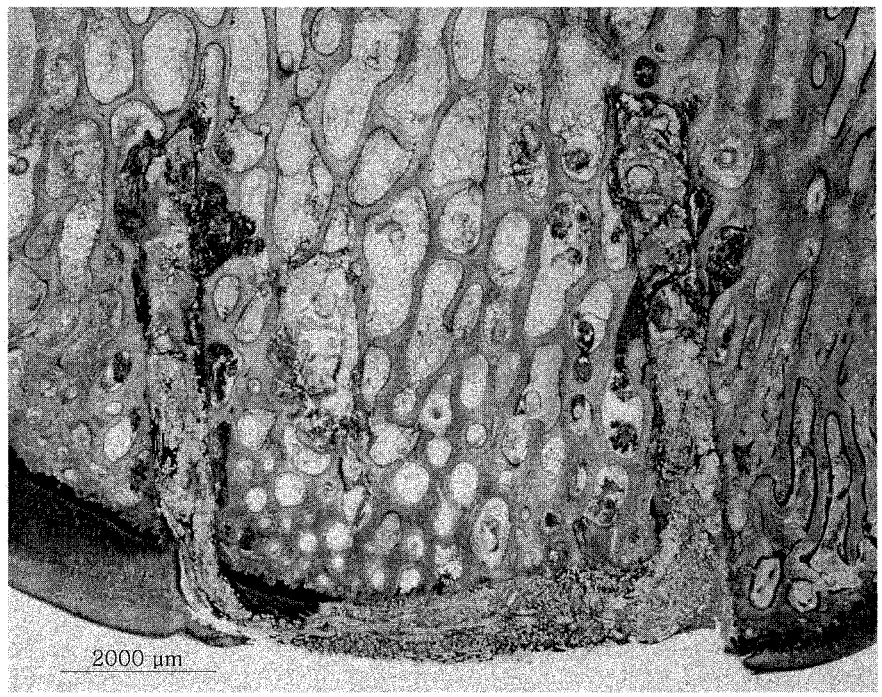
FIG. 20 is a microscopic image of a fifth histologic animal specimen in which the device of FIGS. 1 to 7 has been implanted in the femoral condyle of the knee joint for six weeks.
Figure 21:
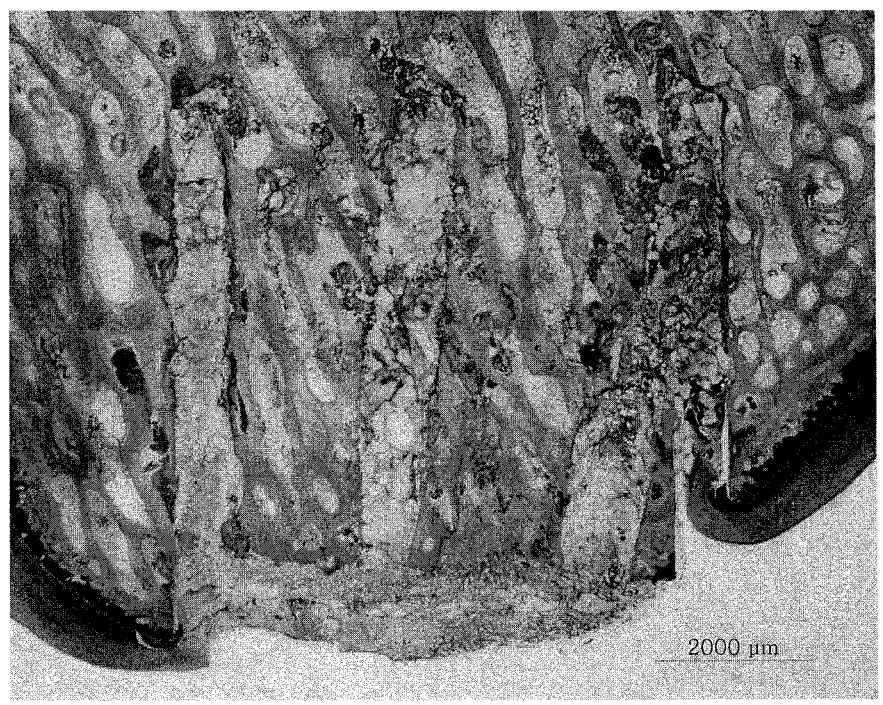
FIG. 21 is a microscopic image of a sixth histologic animal specimen in which the device of FIGS. 1 to 7 has been implanted in the femoral condyle of the knee joint for six weeks.

FIGS. 16 to 21 are microscopic images of a histologic specimen taken from six different animals implanted with the device of FIGS. 1 to 7. FIGS. 16 to 18 were taken after two weeks following implantation and FIGS. 19 to 21 six weeks after implantation. As can be seen, the pad material 102 was retained in the articular cartilage defect space 901 between the subchondral bone surface and the free cartilage surface. The fabric anchor 101 was thoroughly mixed and invaded with loose connective tissue, and was in most parts non-vascularised and only at a few sites loosely vascularised. At the few sites a fibrin mesh was present with sparsely present free cells. The fabric material 101 and inter-fibre spaces 106 were invaded mainly by connective tissue cells. Also free cells were present, such as macrophages and also foreign body giant cells around the mesh material surfaces. The interfibriller spaces were thus filled with mixed materials, consisting of loose collective tissue, composed of fibrous materials and free cells beside resident fibroblast cells as well as areas with bone debris, removed articular cartilage tissue debris as well as fibrin mesh areas. Generally, these tissues were poorly vascularised. Along the vertical, anchoring grooves 900 into the deeper subchondral bone areas, these grooves 900 were all filled with either mesh material 101 and/or similar material as described above. The grooves were generally 8 to 10 millimeter deep, measured from the articular cartilage surface. The anchoring mesh material 101 filled these vertical grooves 900 up to about 4 to 6 millimeters from the surface. The perifibrilla mesh space consists again of either loose connective tissue with resident fibroblast cells and free cells or with debris of cartilage or bone tissue. Also few foreign body giant cells were present.

The articular cartilage defect volume measured from the subchondral bone was estimated subjectively to be filled to a degree roughly of about 50 to 60% with fabric anchor 101 and intermesh biological material. Between the fabric anchor 101, also round types of free cells i.e. lymphocytes were present at some occasions.

The experimental investigation confirmed the cartilage repair device 100 of FIGS. 1 to 7 was retained in situ at both two and six weeks post surgery time points. The interfibriller mesh spaces were filled with loose connective tissue, and fibriller of tissue containing fibroblast cells but also free cells, such a macrofages, foreign body giant cells and lymphocytes. At some locations, cells were absent and just fibrin scaffold was present beside bone tissue debris (from the drilling) as well as cartilage tissue debris from the time of surgery.

The present implantable are also suitable for the repair of other connective tissue than cartilage; for example the rotator cuff at the shoulder. A rotator cuff tear is a serious injury and many attempts have been made to repair it with patch based systems. Such patches as have been used by surgeons were on the whole unsuccessful because they were constructed from processed tissue that could not support sutures which would easily cut through the patch resulting in failed surgical repair.

Figure 22:
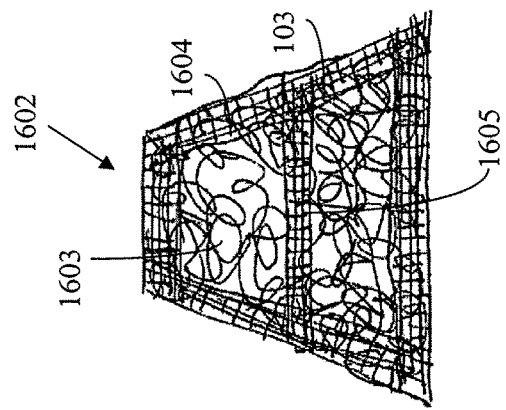
FIG. 22 illustrates various polygonal shaped implantable repair devices in which the main body of the pad is both bordered and bisected by greater density textile strips according to further specific embodiments of the present invention.
Figure 22:
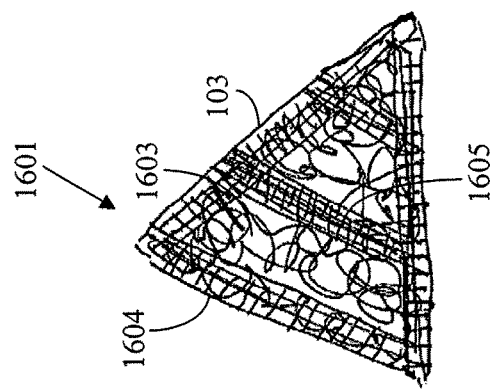
Figure 22:
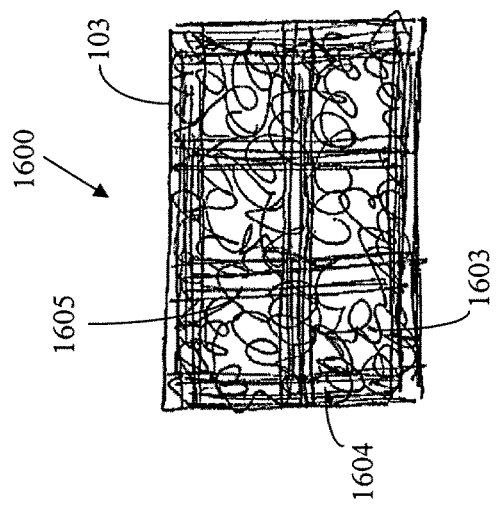

Referring to FIG. 22, the shape of the patch may be square or rectangular 1600, triangular 1601 or trapezoid 1602. The patch 1600, 1601, 1602 comprises a pad 1603 made of the same material as that described with reference to FIGS. 1 to 15 for the repair of cartilage. Additionally, the pad 1603 is reinforced at its perimeter 103 with woven textile strips 1604 integrated to the pad 1603 with fibre entanglements. The main body of the pad 1603 also comprises bisecting strips 1605 attached by the same fibre entanglement. These strips are made from the same material as the anchorage material as described with reference to FIGS. 1 to 15. The presence of such textile strips 1604 at the perimeter permits the patch to be adequately and securely sutured to the surrounding soft tissue, this being muscle or capsule, or tendon like structures. The textile strips 1605 present within the body of the patch reinforces the non-woven structure of the pad 1603 and prevents it from stretching under load until, and after the patch has been ingrown with tissue. The patch 1600, 1601, 1602 can be made of different sizes or of one size with the possibility of trimming at regions defined by the woven strips 1605 to reduce the size as the surgeon requires. The patch can be of a bespoke size and shape as might be defined by a user. Additionally, the woven strip 1604 can be folded around the perimeter 103 of the pad 1603 or just laid flat during the process of needling used to integrate each strip 1604, 1605 to the pad 1603. The size of the construct 1600, 1601, 1602 can be reduced by cutting along one of the edges of the strips 1605 immediately prior to implantation as required. The connective tissue repair device of FIG. 22 does not comprise the anchorage strips or legs for positioning and anchorage within appropriately formed bone grooves. That is, pad 1603 is fixed in position at a repair site and connected to the surrounding soft tissue exclusively by suturing. Alternative means for attachment may also be provided by natural or further synthetic medical cords. This device is intended to bridge the defect in the soft tissue (such as the rotator cuff at the shoulder joint), whereby the device bridges the defect site, and is sutured at its perimeter to the surrounding tissue through the dense textile strips 1604, which can support sutures.

However, according further embodiments, the embodiments of FIG. 22 may also comprise the strip or leg extensions 200, 1200, 1302. Such strips or legs 200, 1200, 1302 may be formed as a continuation of woven strips 1604, 1605 and may extend from one, a plurality or all perimeter edges of the devices 1600, 1601, 1602.

As will be appreciated, the device of FIG. 22 and in particular the pad 1603 and strips 1604, 1605 may be a bioabsorbable or non-bioabsorbable material and may be seeded with cells or generally bioenhanced to encourage integration with the surrounding tissue as described previously.

What is claimed is:

1. An implantable prosthetic cartilage repair device for the repair of damaged cartilage in an animal or a human being, the device consisting essentially of:
    a single synthetic biocompatible pad of a non-woven fabric, the single pad having an open structure formed from entangled fibers to provide a scaffold for the in-growth of tissue into the single pad, wherein the single pad is shaped and dimensioned to occupy a site from which damaged cartilage has been removed; and
    at least one anchor of a woven fabric, the anchor having an upper facing surface, an opposed downward facing surface, and an open structure to provide a scaffold for the in-growth of tissue into the at least one anchor;
    wherein the single pad is positioned on the upper facing surface of the at least one anchor, and the single pad and the at least one anchor are connected together and integrated to form a unitary structure by entanglement of fibers of the single pad with fibers of the at least one anchor; and
    wherein the at least one anchor comprises legs that extend away from a perimeter region of the single pad, each leg having longitudinal edges and being spaced apart relative to one another along their respective lengths such that in an unfolded orientation the longitudinal edges of neighbouring legs are not in contact with one another, the legs being shaped to be introduced into a groove formed in bone around the site from which the damaged cartilage has been removed.

2. The device according to claim 1, wherein the single pad and the at least one anchor comprise enhanced surface properties so as to attract tissue in-growth into the single pad and the at least one anchor.

3. The device according to claim 1, wherein the single pad is in the form of a circular, crescent-shaped, ring shaped, hexagonal or part circular pad.

4. The device according to claim 1, wherein the single pad is bioabsorbable.

5. The device according to claim 1, wherein the single pad is non-bioabsorbable.

6. The device according to claim 1, wherein the single pad is seeded with cells selected from chondrocyte; fibroblasts; mesenchymal progenitor cells; endosteal cells; periosteal cells; and inducible chondroprogenitor cells in extraskeletal organs.

7. The device according to claim 1, wherein the single pad is seeded with disseminated connective tissue removed from a joint or connective tissue from the repair site.

8. The device according to claim 1, wherein the single pad is seeded with autologous cells from the animal, including human being, into which the device is implanted.

9. The device according to claim 1, wherein the at least one anchor comprises holes for tissue and bone ingrowth.

10. The device according to claim 1, wherein the at least one anchor comprises tissue.

11. The device according to claim 1, wherein the single pad and the at least one anchor are formed from the same material.

12. The device according to claim 1, wherein the single pad and the at least one anchor are connected together and integrated by entanglement of their fibers at a central region of the at least one anchor.

13. The device according to claim 1, wherein the at least one anchor has a sheet or strip-structure.

14. The device according to claim 1, in which the device is movable between the unfolded orientation and a folded implantation orientation, and in which the legs are arranged around substantially the entire perimeter region of the single pad, each leg extending away from a different part of the perimeter region.

15. The device according to claim 14, wherein, in the folded implantation orientation, the device adopts a substantially tubular shape in which the legs of the implant together define a substantially continuous wall of the device.

16. The device according to claim 14, wherein, in the folded implantation orientation, the legs extend substantially perpendicularly relative to a plane of the single pad.

17. The device according to claim 16, wherein, in the folded implantation orientation, each leg is separated from each neighbouring leg by a gap region.

18. A method of manufacturing an implantable prosthetic cartilage repair device for the repair of damaged cartilage in an animal or a human being, the method consisting essentially of:
providing a single synthetic biocompatible pad of a non-woven fabric, the single pad having an open structure formed from entangled fibers to provide a scaffold for the in-growth of tissue into the single pad, the single pad being shaped and dimensioned to occupy a site from which damaged connective tissue has been removed;
providing at least one textile anchor of a woven fabric, the anchor having an upper facing surface, an opposed downward facing surface, and an open structure to provide a scaffold for the in-growth of tissue into the at least one anchor; and
positioning the single pad on the upper facing surface of the at least one anchor, and connecting the at least one anchor to the single pad to form an integrated unitary structure by entangling fibers of the single pad with fibers of the at least one anchor;
wherein the at least one anchor comprises legs that extend away from a perimeter region of the single pad, each leg having longitudinal edges and being spaced apart relative to one another along their respective lengths such that in an unfolded orientation the longitudinal edges of neighbouring legs are not in contact with one another, the legs being shaped to be introduced into a groove formed in bone around the site from which the damaged cartilage has been removed.

19. The method according to claim 18, wherein the legs of the at least one anchor are created by cutting sections of the at least one anchor to create a spatial gap between the longitudinal edges of neighbouring legs.

20. The method according to claim 18, wherein the device is arranged so that it is movable between the unfolded orientation and a folded implantation orientation, and wherein the legs are arranged around substantially the entire perimeter region of the single pad, with each leg extending away from a different part of the perimeter region.

* * * * *